United States Patent
Adkins, Jr. et al.

(10) Patent No.: US 10,959,940 B2
(45) Date of Patent: Mar. 30, 2021

(54) ANTI-ALLERGENIC OCULAR COMPOSITIONS AND EYELID CLEANSING WIPES

(71) Applicant: OCuSOFT, Inc., Rosenberg, TX (US)

(72) Inventors: Nat Adkins, Jr., Richmond, TX (US); Troy Smith, Richmond, TX (US); Paramita Sarkar, Richmond, TX (US)

(73) Assignee: OCuSOFT INC., Rosenberg, TX (US)

( * ) Notice: Subject to any disclaimer, the term of this patent is extended or adjusted under 35 U.S.C. 154(b) by 0 days.

(21) Appl. No.: 16/508,626

(22) Filed: Jul. 11, 2019

(65) Prior Publication Data

US 2020/0016071 A1    Jan. 16, 2020

Related U.S. Application Data

(60) Provisional application No. 62/697,213, filed on Jul. 12, 2018.

(51) Int. Cl.
| | | |
|---|---|---|
| *A61K 9/00* | (2006.01) | |
| *A61K 31/133* | (2006.01) | |
| *A61K 9/70* | (2006.01) | |
| *A61K 31/015* | (2006.01) | |
| *A61K 31/353* | (2006.01) | |

(52) U.S. Cl.
CPC .......... *A61K 9/0048* (2013.01); *A61K 9/7007* (2013.01); *A61K 31/015* (2013.01); *A61K 31/133* (2013.01); *A61K 31/353* (2013.01)

(58) Field of Classification Search
None
See application file for complete search history.

(56) References Cited

U.S. PATENT DOCUMENTS

| | | | |
|---|---|---|---|
| 9,078,872 B2 * | 7/2015 | Erfurt | A23L 3/3508 |
| 2005/0232953 A1 * | 10/2005 | Barnikol | A61Q 19/02 |
| | | | 424/400 |
| 2012/0128754 A1 | 5/2012 | Wei | |
| 2014/0161903 A1 | 6/2014 | Chapin et al. | |
| 2014/0315995 A1 * | 10/2014 | Dreher | A61K 31/197 |
| | | | 514/458 |
| 2017/0189325 A1 | 7/2017 | Wilson et al. | |

FOREIGN PATENT DOCUMENTS

| | | | |
|---|---|---|---|
| KR | 10-1006693 B1 | | 1/2011 |
| KR | 101006693 B1 * | | 1/2011 |
| TW | 201532621 A | | 9/2015 |

OTHER PUBLICATIONS

Camille G. Wermuth, Similarity in drugs: reflections on analogue design, 2006, Drug Discovery Today, vol. 11, pp. 348-354 (Year: 2006).*
Merriam-Webster Online http://www.merriam-webster.com/cgi-bin/dictionary?book=Dictionary&va=derivative (Year: 2008).*
"What you should know about the efficacy, selection and extended functions of eye cream, Aug. 23, 2016." excerpted from https://www.bella.tw/articles/skincare/9501, Apr. 15, 2020.

\* cited by examiner

*Primary Examiner* — Abigail Vanhorn
*Assistant Examiner* — Ali S Saeed
(74) *Attorney, Agent, or Firm* — D'Ambrosio & Menon, PLLC; Usha Menon

(57) ABSTRACT

An anti-allergenic composition comprising from about 0.01% to about 50% by weight of a polyphenol, from about 0.01% to about 50% by weight of a terpene compound, and from about 0.001% to about 10% by weight of a glycolipid. The polyphenol has a flavanol derivative. The terpene compound can be selected from the group consisting of a terpene, terpinene, a terpene derivative and combinations thereof. In an embodiment, the sphingolipid comprises about 0.2% phytosphingosine.

8 Claims, No Drawings

ANTI-ALLERGENIC OCULAR COMPOSITIONS AND EYELID CLEANSING WIPES

CROSS REFERENCE TO RELATED APPLICATION

This application claims the benefit of Provisional U.S. Patent Application No. 62/697,213, filed Jul. 12, 2018, the entire content and disclosure of which, both express and implied, is incorporated herein by reference.

FIELD OF THE INVENTION

The invention relates generally to compositions and more particularly to an anti-allergenic composition for alleviating the symptoms associated with eyelid allergy.

BACKGROUND

Ocular health refers to eyes as well as structures associated with the eyes, eyelids for example. The eyelids are important in over-all ocular health because they protect the eyes from dangers such as approaching objects or from airborne contaminants, such as pollen, dust particles or other foreign bodies. The eyelids contain essential glands; the lacrimal glands and meibomian glands that produce layers of tear film that are critical for healthy eyes. When an individual blinks, a new tear film is created and tears are distributed across the cornea to lubricate the surface of the eye. This blinking action also "flushes" foreign materials from the eye.

The eyelids, however, are subject to allergies and bacterial infection of the surface of the skin. Seasonal allergies can also cause red, itchy, irritated eyes and eyelids. Allergy eye drops relieve eye symptoms but do not calm the irritated eyelids. Therefore, there is a need for a product that can alleviate the symptoms associated with allergic conditions of the eyelids.

SUMMARY

An anti-allergenic composition is provided, the composition comprising: from about 0.01% to about 50% by weight of a polyphenol, from about 0.01% to about 50% by weight of a terpene compound, and from about 0.001% to about 10% by weight of a glycolipid. The polyphenol has a flavanol derivative. The flavanol derivative can be selected from the group consisting of catechin, epigallocatechin and epigallocatechin gallate. The terpene compound can be selected from the group consisting of a terpene, terpinene, a terpene derivative and combinations thereof. The glycolipid can be selected from the group consisting of sphingolipid, ceramide, glycerophopspholipids, a sphingolipid derivative and combinations thereof. In an embodiment, the sphingolipid comprises about 0.2% phytosphingosine.

DETAILED DESCRIPTION

The term and phrases "invention," "present invention," "instant invention," and similar terms and phrases as used herein are non-limiting and are not intended to limit the present subject matter to any single embodiment, but rather encompass all possible embodiments as described.

As used herein, all weight percentages (wt. %) are based on the total wt. % of the anti-allergenic composition, unless otherwise specified. Additionally, all composition percentages are based on totals equal to 100 wt. %, unless otherwise specified.

The compositions, products, kits and methods described herein can "comprise," "consist essentially of," or "consist of" any of the ingredients or steps disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and can include the ingredients/steps of the present invention and do not exclude other ingredients or steps described herein. The use of the word "a" or "an" when used in conjunction with the term "comprising" in the claims and/or the specification may mean "one," but it is also consistent with the meaning of "one or more," "at least one," and "one or more than one." As used herein, "consisting essentially of" means that the invention may include ingredients/steps in addition to those recited in the claim, but only if the additional ingredients do not materially alter the basic and novel characteristics of the claimed invention. Generally, any additives may not be present at all or only in trace amounts. However, it may be possible to include up to about 10% by weight of materials that could materially alter the basic and novel characteristics of the invention as long as the utility of the composition (as opposed to the degree of utility) is maintained.

All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. In one non-limiting embodiment the terms are defined to be within 5%, more preferably within 1%, and most preferably within 0.5%. The term "substantially" and its variations are defined as being largely but not necessarily wholly what is specified as understood by one of ordinary skill in the art, and in one non-limiting embodiment substantially refers to ranges within 0.5%-5%.

As used herein, the term "effective amount" of a composition refers to an amount sufficient to elicit the desired biological response. As will be appreciated by those of ordinary skill in this art, and effective amount of a substance may vary depending on such factors as the desired biological endpoint, the patient, etc. In some embodiments, a therapeutically effective amount of a composition is an amount that is sufficient, when administered to a subject suffering from or susceptible to a disease, disorder, and/or condition, to treat, inhibit, reduce, prevent, and/or delay the onset of one or more symptoms of eyelid allergy. The terms "treat" or "reduce" or any variation of these terms includes a qualitative or quantitative decrease in allergy symptoms. For example, the effective amount/therapeutically effective amount of the composition to treat eyelid allergy is the amount that alleviates, ameliorates, relieves, inhibits, prevents, delays onset of, reduces severity of and/or reduces incidence of one or more symptoms or features associated with allergic conditions of the eyelids.

In one embodiment, an anti-allergenic composition is disclosed. All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. In one non-limiting embodiment the terms are defined to be within 5%, more preferably within 1%, and most preferably within 0.01%. The term "substantially" and its variations are defined as being largely but not necessarily wholly what is specified as understood by one of ordinary skill in the art, and in one non-limiting embodiment substantially refers to ranges within 0.01%-5%.

The anti-allergenic composition can include anti-inflammatory, anti-microbial, anti-fungal and anti-irritant agents. In one embodiment, the composition is an eyelid cleanser for removing pollen, contaminants and allergens from the eyelids and eyelid margins/areas surrounding the eyes/eyelids. The composition can be configured to prevent or reduce eyelid allergy-like symptoms, namely, redness, itching, roughness, or inflammation of the eyelids or its surrounding areas. The composition has an effective amount of: one or more plant extracts, a lipophilic or amphiphilic agent, a preservative with anti-microbial activity, and a suitable solvent or carrier.

The plant extracts can be selected from a group consisting of Camellia Sinensis (green tea), Melaleuca alternifolia (tea tree) oil, *Citrus sinensis*, chamomile flowers, and combinations thereof. In one specific embodiment, the plant extract can include a mixture of green tea extract and tea tree oil. The selected plant extracts will contain an effective amount (i.e., at least a 0.01% w/w of the composition) of a polyphenol and a terpene compound. Such plant extracts typically have anti-microbial, anti-fungal and/or anti-inflammatory activity.

For example, certain Camellia Sinensis or green tea extracts have been shown to contain a polyphenol. The polyphenol can include a flavanol derivate. Flavanol derivatives can include catechin, epigallocatechin and epigallocatechin gallate. Green tea extracts generally have an antioxidant effect that can protect the skin from the damaging effect of free radicals. In addition, certain green tea extracts contain an anti-inflammatory agent that reduces inflammation in the skin. Some green tea extracts have also been shown to have a moisturizing effect and to serve as an inhibitor of epidermal collagenase (a collagen-reducing enzyme that breaks down collagen) to assist in maintaining a firm and elastic skin.

Tea tree oil can generally be obtained by steam distillation from the Australian native plant Melaleuca alternifolia, and contains around a hundred components, such as, terpinenes, terpenes, and related derivatives and combinations. More specifically, tea tree oil often contains monoterpenes, sesquiterpenes and related alcohols.

One important aspect of the composition is related to its anti-microbial activity typically rendered by one or more anti-microbial agents. In an embodiment, the composition includes a glycolipid. The glycolipid can be selected from the group consisting of sphingolipids, ceramides, glycerophospholipids, sphingolipid derivative and combinations thereof. In an embodiment, a sphingoid base, selected from a group consisting of sphingosine, sphinganine, phytosphingosine, a phytosphingosine salt, tetraacetyl-phytosphingosine, N-acetylphytosphingosine and mixtures thereof is selected. In one specific embodiment, the sphingoid base includes about 0.1% to about 0.3% phytosphingosine and/or phytosphingosine hydrochloride (HCl). Phytosphingosine HCl is a natural, skin-identical active ingredient. Phytosphingosine and Phytosphingosine HCl can inhibit the growth of microorganisms on the skin, reduce redness and inflamed skin and are active at very low concentrations. Phytosphingosine (PSG) is also a water-binding agent that mimics the natural lipid layer of the outer epidermis to increase the moisturizing of the skin. Beneficially, PSG has both anti-bacterial and wound-healing properties and it acts as an anti-inflammatory at concentrations as low as 0.1%. Some embodiments of the anti-allergenic composition include PSG which is esterified with salicylic acid and/or its derivatives. Salicyloyl PSG is a derivative of the naturally occurring skin-identical PSG which is covalently coupled with salicylic acid. Salicyloyl PSG and its derivatives contribute to the prevention of loss of moisture from the skin and boosting collagen synthesis while reducing its degradation, and soothing inflamed skin.

Preferred embodiments of the composition can include a preservative having an effective anti-microbial activity. One such preservative with significant anti-microbial properties is polyaminopropyl biguanide (PAPB) which is pseudonymous for polyhexamethylene biguanide (PHMB), and polyhexamethylene biguanide hydrochloride.

In addition, a 1,2-diol can be included in the composition for its anti-microbial enhancing activity. Preferred 1,2-diols are selected from the group consisting of 1,2-hexanediol, 1,2-octanediol, 1,2-decanediol, and mixtures thereof. 1,2-hexanediol is a synthetic preservative with a broad spectrum anti-microbial activity. Similarly, 1,2-octanediol (also known as caprylyl glycol) is another active substance which functions as a preservative and anti-microbial. For example, the combination of the preservative polyaminopropyl biguanide, 1,2-hexanediol, and 1,2-octanediol operates to synergistically enhance the anti-microbial effect of the composition.

A blend of one or more surfactants may also be included in the anti-allergenic composition. Various surfactants may be included in the composition to achieve a desired foaming capacity and/or cleansing capability. The inclusion of a surfactant will enhance the ability of the composition to dissolve and remove oil, antigens, debris and desquamated skin. Preferable surfactants have a foaming ability and include nonionic or amphoteric surfactants having a HLB value between 10 and 18. If more than one surfactant is used, then at least one surfactant should have an HLB value between 10 and 18 and the other surfactant(s) should either have an HLB between 10 and 18 or an HLB value between 5 and 10.

Suitable surfactants can include amphoteric surfactants, anionic surfactants, and nonionic surfactants. Suitable amphoteric surfactants include, but are not limited to alkyldimethyl betaines, alkylamido betaines, sulfobetaines, and imidazoline amphoterics. Suitable anionic surfactants include, but are not limited to fatty alcohol sulfates, alpha olein sulfonates, sulfosuccinates, sarcosinates, phosphate esters, and carboxylates. Suitable nonionic surfactants include, but are not limited to alkanolamides, ethoxylated amides, esters, alkylated alcohols, alkylpolyglucosides, amine oxides, sorbitan esters, and ethoxylates.

The one or more surfactants may include, but are not limited to, sorbitan esters (e.g. Span 20 or sorbitan monolaurate), polyethylene glycol (PEG) modified surfactants (e.g. polysorbate 20, Brij 52, PEG-75 Lanolin), modified phospholipids, modified sugars (e.g., alkyl polyglucosides, fatty acid glucamides), amineoxides, and/or block copolymers such as Pluronics (Pluronic F120) or tyloxapol. The total concentration of surfactants will be in the range of 0.1 to 20% w/w of the final formulation but, more preferably in the 0.5-5% range. The inclusion of a surfactant can increase the cleansing ability of the composition and provide it with a foaming capability. Foams are considered to have optimal cleansing capability.

Although optional, a foam stabilizer may also be added to the composition, and may include, without limitation, a polyethylene glycol diester of methyl glucose and a fatty acid. The fatty acid can be selected from a group consisting of oleic acid, stearic acid, lauric acid, caprylic acid, and capric acid. Preferably, the one or more foam stabilizers includes PEG-120 methyl glucose dioleate.

One or more moisturizers, emollients, humectants, or lubricants are also commonly added to the composition and are generally referred to herein as moisturizers. Suitable moisturizers are propylene glycol, glycerin, polyethylene glycol (e.g. PEG 300, 400, 600) or generally, liquid polyols, nut oils and derivatives, rose water (floral extracts), cucumber extract, fruit extracts, sodium alginate, hyaluronic acid, diglyceride, triglyceride, PEG-75 lanolin, mineral oil, and silicone oil.

Additional optional components may also be added to the composition in amounts up to a 5% w/w of the composition. These optional components include such compounds as skin conditioning agents (e.g., D-panthenol), antioxidants (e.g., Vitamin E and its derivatives, green tea extract, Vitamin C and its derivatives), anti-irritating/soothing agents (e.g., allantoin, aloe vera, tea tree oil), cooling agents (e.g., sorbitol, xylitol, menthol, thymol), viscosity modifiers (e.g., carboxymethycellulose, hypromellose, carbopol), and nutrients (e.g., minerals, vitamins, amino acids or polypeptides).

The composition is substantially non-irritating to the eye. Advantageously, the composition does not contain astringents such as, zinc or zinc salts.

The composition can be selected from a group consisting of a solution, a mist, a foam, a gel, a spray, a lotion, a suspension, an emulsion, an ointment and combinations thereof.

In one embodiment, the composition may be combined with a suitable substrate to form an anti-allergenic product for cleansing the eyelids. The substrate can be impregnated with a clinically effective amount of the composition. The substrate can be a wipe, a fabric pad or a towelette. The anti-allergenic product can be configured as a single use product.

In another embodiment, a kit containing one or more fabric pads or wipes impregnated/pre-moistened with the composition is disclosed. The term "pad" refers to a thick piece of fabric that is capable of holding or absorbing the composition. For example, the fabric can be a lint-free fabric, such as, rayon or another suitable material. In certain embodiments, the fabric pad may be a cotton pad. The fabric pad can comprise a textured surface. The pads may be single use disposable pads. The kit can include between 1-100 pads. The pads may be sealed within suitable packaging.

In certain embodiments, the kit can include one or more single use dry pads and a dispenser containing the composition. A desired amount of the composition may be then applied to a dry pad prior to using it to cleanse the eyelids.

In another embodiment, a method for treating eyelid allergy involves providing an anti-allergenic composition having from about 0.01% to about 50% by weight of a polyphenol, from about 0.01% to about 50% by weight of a terpene compound, and from about 0.001% to about 10% by weight of a glycolipid. The composition is in the form selected from a group consisting of a wipe, a spray, a mist, a foam or a gel. The method further involves applying the composition to an eyelid surface and/or an area surrounding the eyelid to relieve redness, discomfort and irritation in and around the eyelids. The composition can be configured as a non-residue forming composition. The composition can be left on the eyelid or rinsed off with water. The composition can clean and remove foreign material and debris from the application site including microorganisms, such as, bacteria or allergens on the eyelids. It can also induce foaming, which assists in the cleansing ability of the formulation and prevent allergies and promote anti-inflammation and redness of the eyelids and eyelid margins.

The present invention can comprise or consist essentially of the components as well as other components which are not recited (such as, biological gloves).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

We claim:

1. An anti-allergenic composition consisting of:
   from about 0.01% to about 50% by weight of a polyphenol,
   from about 0.01% to about 50% by weight of a terpene compound, and
   about 0.2% phytosphingosine.

2. The anti-allergenic composition according to claim 1, wherein the polyphenol is a flavanol derivative.

3. The anti-allergenic composition according to claim 2, wherein the flavanol derivative is selected from the group consisting of catechin, epigallocatechin and epigallocatechin gallate.

4. A method for treating eyelid allergy, comprising: applying the anti-allergenic composition of claim 1 to an eyelid surface and/or an area surrounding the eyelid.

5. The method according to claim 4, wherein the applying is done to relieve redness, discomfort and irritation in and around the eyelids.

6. The method according to claim 4, wherein the polyphenol is epigallocatechin gallate.

7. The method according to claim 4, wherein the composition is a non-residue forming composition.

8. The method according to claim 4, wherein the composition is configured as a leave-on or a rinse-off composition.

* * * * *